(12) United States Patent
Blate et al.

(10) Patent No.: US 12,194,208 B2
(45) Date of Patent: Jan. 14, 2025

(54) GERMICIDAL PARTITION SYSTEM

(71) Applicant: AURA Technologies, LLC, Raleigh, NC (US)

(72) Inventors: Alex Blate, Chapel Hill, NC (US); Greg Houlgate, Carlsbad, CA (US); Anna Bennett, Chapel Hill, NC (US); Garrett Goss, Morrisville, NC (US); Matthew Feurer, Franklin Lakes, NJ (US)

(73) Assignee: AURA Technologies, LLC, Carrboro, NC (US)

( * ) Notice: Subject to any disclaimer, the term of this patent is extended or adjusted under 35 U.S.C. 154(b) by 0 days.

(21) Appl. No.: 18/395,949

(22) Filed: Dec. 26, 2023

(65) Prior Publication Data

US 2024/0131215 A1 Apr. 25, 2024

Related U.S. Application Data

(60) Continuation-in-part of application No. 18/205,834, filed on Jun. 5, 2023, now Pat. No. 11,857,707, which (Continued)

(51) Int. Cl.
*A61L 9/22* (2006.01)

(52) U.S. Cl.
CPC ............ *A61L 9/22* (2013.01); *A61L 2209/111* (2013.01); *A61L 2209/15* (2013.01)

(58) Field of Classification Search
CPC .................................... A61L 9/22; A61L 2/14
See application file for complete search history.

(56) References Cited

U.S. PATENT DOCUMENTS

| 4,829,398 A | 5/1989 | Wilson |
| 6,565,035 B1 * | 5/2003 | Kim ...................... B64D 13/00 |
| | | 454/192 |

(Continued)

FOREIGN PATENT DOCUMENTS

| CN | 2930718 Y | 8/2007 |
| CN | 101640383 A | 2/2010 |

(Continued)

OTHER PUBLICATIONS

International Search Report for PCT/US2021/025755, Aug. 6, 2021, 2 pages.

(Continued)

*Primary Examiner* — Donald R Spamer
(74) *Attorney, Agent, or Firm* — Danielson Legal LLC

(57) ABSTRACT

Systems and methods for creating a germicidal partition. A germicidal partition system including at least one negative ion generator including at least one negative high-voltage source, at least one high-voltage conductor electrically connected to the at least one negative high-voltage source, and at least one anode electrically connected to the at least one high-voltage conductor, and at least one fan configured to draw air into the system, direct the air through the at least one negative ion generator, and output the air through at least one manifold, wherein the air outputted through the at least one manifold is configured to create a barrier between a first air mass and a second air mass, such that the outputted air reduces at least one of the transfer of contaminants or the concentration of viable contagions between the first air mass and the second air mass.

16 Claims, 9 Drawing Sheets

Related U.S. Application Data is a division of application No. 17/665,904, filed on Feb. 7, 2022, now Pat. No. 11,690,931, which is a continuation of application No. PCT/US2021/025755, filed on Apr. 5, 2021.

(60) Provisional application No. 63/109,192, filed on Nov. 3, 2020, provisional application No. 63/106,861, filed on Oct. 28, 2020, provisional application No. 63/005,124, filed on Apr. 3, 2020.

(56) References Cited

U.S. PATENT DOCUMENTS

| | | | |
|---|---|---|---|
| 2004/0047775 | A1 | 3/2004 | Lau et al. |
| 2008/0014851 | A1 | 1/2008 | Takayanagi |
| 2008/0193328 | A1 | 8/2008 | Crapser |
| 2014/0363333 | A1 | 12/2014 | Carr |
| 2016/0218490 | A1* | 7/2016 | Nishida ............ A61L 9/22 |
| 2016/0263261 | A1* | 9/2016 | Trapani ............ A61L 2/202 |
| 2019/0374985 | A1 | 12/2019 | Ko et al. |
| 2022/0160926 | A1* | 5/2022 | Blate ............ A61L 9/22 |

FOREIGN PATENT DOCUMENTS

| | | |
|---|---|---|
| CN | 106482276 A | 3/2017 |
| CN | 206483002 U | 9/2017 |
| EP | 1982345 B1 | 7/2015 |
| JP | 2003332023 A | 11/2003 |
| JP | 2011030719 A | 2/2011 |
| JP | 2011168159 A | 9/2011 |
| JP | 202229347 U | 5/2012 |
| JP | 2014136045 A | 7/2014 |
| KR | 20110052006 A | 5/2011 |

OTHER PUBLICATIONS

Written Opinion for PCT/US2021/025755, Aug. 6, 2020, 6 pages.
California Air Resources Board, "List of CARB-Certified Air Cleaning Devices." Indoor Air Quality Group, available at https://ww2.arb.ca.govlist-carb-certified-air-cleaning devices.
Bailey, William H. et al. "Exposure of laboratory animals to small air ions: a systematic review of biological and behavioral studies." BioMedical Engineering OnLine, 17, Article No. 72 (2018).
Office Action for Chinese Pat. Appl. No. 202180007605.1, Aug. 4, 2023. 8 pages.
Office Action for Canadian Pat. Appl. No. 3,168,735. Oct. 26, 2023. 7 pages.
Extended European Search Report for EP. Appl. No. 21781822.8. Dec. 19, 2023. 10 pages.
Office Action for Chinese Pat. Appl. No. 202180007605.1, Jan. 29, 2024. 6 pages.
Office Action for Chinese Pat. Appl. No. 202180007605.1, Apr. 30, 2024. 7 pages.

* cited by examiner

GERMICIDAL PARTITION SYSTEM

CROSS-REFERENCE TO RELATED APPLICATIONS

The present application is a continuation-in-part of U.S. patent application Ser. No. 18/205,834, filed on Jun. 5, 2023, which is a division application of U.S. patent application Ser. No. 17/665,904, filed on Feb. 7, 2022, which is a continuation of International (PCT) Patent Application No. PCT/US2021/025755, filed internationally on Apr. 5, 2021, and claims the benefit of and priority to U.S. provisional application No. 63/005,124, filed on Apr. 3, 2020; U.S. provisional application No. 63/106,861, filed on Oct. 28, 2020; and U.S. provisional application No. 63/109,192, filed on Nov. 3, 2020, the entire disclosure of each of which is hereby incorporated by reference as if set forth in its entirety herein.

TECHNICAL FIELD

Embodiments described herein relate to methods and systems for a germicidal partition system and, more particularly but not exclusively, to methods and systems for reducing the transfer of contaminants or viable contagions between two air masses with negatively ionized air.

BACKGROUND

Airborne aerosolized particles are a common vector for person-to-person disease transmission. For example, it has been shown that active COVID-19 virus particles known as virions can remain suspended in air for tens of minutes to hours; these aerosols are expelled by infected persons during normal respiration, talking, singing, coughing, etc. More generally, pathogens, such as microbes, bacteria, and viruses (collectively, "microbes") are spread via airborne transmission. Shared or public indoor spaces, such as hallways, hotels, office buildings, and elevators, can harbor the collective aerosols from many individuals for tens of minutes to hours, depending on ventilation. These aerosols may transfer across shared indoor spaces, through shared ventilation systems, and from people acting as moving microbe vectors.

It is desirable to reduce the transfer of pathogens and pathogen-bearing air between the adjoining areas separated by a portal, such as a doorway. One known method of reducing air transfer is to create a pressure gradient across the portal, ensuring that airflow is unidirectional. This method can be impractical, particularly for retrofitting existing buildings.

Air curtains can also be used to reduce air transfer. Air curtains are fan-powered devices that create invisible barriers over doorways to efficiently separate two different environments, without limiting access by people or vehicles. Air curtains can divide environments to keep two rooms at different temperatures, prevent wind draughts, prevent pests and insects from entering a building, and create a barrier to prevent circulation of dust, pollutants, and odors.

Due to their size, power consumption, operating noise, high air velocity, and human factors, air curtains are typically not used in consumer or residential settings and do not disinfect or neutralize microbes in the air or on people and objects passing through or proximate to the air curtain barrier. The air curtain does not necessarily prevent bacteria or viruses from passing through the barrier. A need therefore exists for methods and systems to improve partition systems.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a germicidal partition system. In some embodiments, the germicidal partition system includes at least one negative ion generator including at least one negative high-voltage source, at least one high-voltage conductor electrically connected to the at least one negative high-voltage source, and at least one anode electrically connected to the at least one high-voltage conductor; and at least one fan configured to draw air into the system, direct the air over or past at least one anode, and output the air through at least one manifold, wherein the air outputted through the at least one manifold is configured to create a barrier between a first air mass and a second air mass, such that the outputted air reduces at least one of the transfer of contaminants or the concentration of viable contagions between the first air mass and the second air mass.

In some embodiments, the germicidal partition system includes at least one negative ion generator including at least one negative high-voltage source, at least one high-voltage conductor electrically connected to the at least one negative high-voltage source, and at least one anode electrically connected to the at least one high-voltage conductor; and at least one fan configured to draw air into the system, direct the air through the at least one negative ion generator, and output the air through at least one manifold, wherein the air outputted through the at least one manifold is configured to create a barrier between a first air mass and a second air mass, such that the outputted air reduces at least one of the transfer of contaminants or the concentration of viable contagions between the first air mass and the second air mass.

In some embodiments, the system is mounted above a doorway or portal or on a ceiling. In some embodiments, the outputted air subtends a majority of the width of the doorway or portal and extends downward for at least four feet.

In some embodiments, the system further comprises at least a first sensor in communication with a control system, such that the control system is configured to alter a state of at least one of the at least one fan or the at least one negative ion generator when the sensor receives a stimulus. In some embodiments, the stimulus is at least one of a motion stimulus or a sound stimulus. In some embodiments, upon receiving the stimulus, the control system activates the fan(s) and/or ion generator(s) for a set duration of time and, once the duration of time has lapsed, the control system deactivates the fan.

In some embodiments, the system is configured to output the air with an ozone concentration less than 0.01 parts per million higher than the concentration of ozone in ambient air.

In some embodiments, the system does not require a filter to maintain ozone safety and neutralize ozone that would otherwise be emitted by an ionizer. In some embodiments, ozone safety will not degrade over time due to exhaustion of filter media.

In some embodiments, the at least one manifold is attached to the at least one anode; and the at least one manifold is removably attached to the system, such that the at least one manifold can be removed with the at least one anode from the system and cleaned or exchanged with at least one replacement manifold and at least one replacement anode.

In some embodiments, the system is configured to be portable and worn on a garment.

In some embodiments, the air outputted through the at least one manifold is laminar; and the air outputted through the at least one manifold comprises at least 1 million negative air ions per cubic centimeter of air.

In some embodiments, acoustic noise produced by the system during operation is less than 55 dBA.

In some embodiments, the system is powered by at least one of by mains AC, a battery, or any combination thereof.

In some embodiments, the air outputted through the at least one manifold has a net cross-sectional shape of at least one of a polygon, circle, ellipse, or oval.

In some embodiments, the system does not comprise a filter.

In another aspect, embodiments relate to a method of creating a germicidal partition. In some embodiments, the method includes receiving, through a fan, air from an ambient environment; directing the air over at least one negative ion generator comprising at least one negative high-voltage source, at least one high-voltage conductor electrically connected to the at least one negative high-voltage source, and at least one anode electrically connected to the at least one high-voltage conductor; and outputting the air through at least one manifold, wherein the air outputted through the at least one manifold is configured to create a barrier between a first air mass and a second air mass, such that the outputted air reduces at least one of the transfer of contaminants or the concentration of viable contagions between the first air mass and the second air mass.

In some embodiments, the air outputted through the at least one manifold maintains a concentration of at least 1 million negative air ions per cubic centimeter of air for a distance of at least four feet from the at least one manifold.

In some embodiments, the air outputted through the at least one manifold is laminar.

In some embodiments, the air outputted through the at least one manifold comprises at least 1 million negative air ions per cubic centimeter of air.

In yet another aspect, embodiments relate to a method of building a germicidal partition system. In some embodiments, the method includes electrically connecting at least one high-voltage conductor to at least one negative high-voltage source and at least one anode, wherein the at least one high-voltage conductor, the at least one negative high-voltage source, and the at least one anode comprise a negative ion generator; and connecting the negative ion generator to a fan configured to draw air into the system, direct the air over the at least one anode, and output the air through at least one manifold, wherein: the air outputted through the at least one manifold is configured to create a barrier between a first air mass and a second air mass, such that the outputted air reduces at least one of the transfer of contaminants or the concentration of viable contagions between the first air mass and the second air mass.

In some embodiments, the air outputted through the at least one manifold is a negatively charged laminar air curtain.

According to one aspect, embodiments relate to a germicidal partition system. In some embodiments, the germicidal partition system includes at least one negative ion generator including at least one negative voltage source configured to produce a potential between −3 kV and −10 kV and sufficient to produce negatively ionized air with a negative air ion concentration of at least 1 million negative air ions per cubic centimeter of air, and configured to produce a net increase in ozone concentration between zero and 0.01 parts per million; at least one voltage conductor electrically connected to the at least one negative voltage source; at least one output manifold; a plurality of anodes distributed along at least a portion of the at least one output manifold and electrically connected to the at least one voltage conductor; and at least one fan configured to draw air into the system; direct the air into the at least one output manifold and past the plurality of anodes to create the negatively ionized air; and output the negatively ionized air through the at least one manifold, wherein the negatively ionized air outputted through the at least one manifold creates a barrier between a first air mass and a second air mass, such that the outputted negatively ionized air reduces at least one of the transfer of contaminants or the concentration of viable contagions between the first air mass and the second air mass.

In some embodiments, the system is operably positioned with respect to a lavatory or urinal, and configured such that air velocity at an opening of the lavatory or urinal is sufficient to contain at least some aerosols generated during flushing of the lavatory or urinal within said lavatory or urinal or push said aerosols onto a surface of the lavatory, urinal, floor, or into water in the lavatory or urinal.

In some embodiments, the system further includes: at least one sensor, at least one control system, and at least one annunciator, wherein: the at least one sensor is in operable communication with the at least one control system, the at least one control system is in operable communication with the at least one annunciator, and the at least one control system is configured to configure the annunciator into a first state upon receiving a stimulus, and configure the annunciator into a second state upon expiration of a specified time duration.

In some embodiments, the at least one sensor is configured to be stimulated by at least one of motion, proximity, sound, contact, a switch, a digital signal, an analog signal, a radio or radio frequency signal, light, imagery, or processed imagery.

In some embodiments, the system is configured to mechanically or electrically connect with or to communicate with a second system.

In some embodiments, the first air mass comprises air inside a transportation device and the second air mass comprises air outside of the transportation device. In some embodiments, the transportation device is an elevator.

In some embodiments, the system further comprises at least a first door position sensor in communication with a control system to monitor a position of a door of the transportation device and configured to, upon detecting that the door has been closed for a specified duration of time, alter a state of at least one manifold, a vane or diverter, or a diffuser, such that at least some of the negatively ionized air output is directed away from the door. In some embodiments, the system is configured to create a barrier between a first designated sitting or standing area and a second designated sitting or standing area.

In some embodiments, the system in installed above, adjacent to, or proximate to a point-of-sale (POS) location or workstation, and the first air mass is the air mass on a first side of the POS and the second air mass is the air mass on a second side of the POS or workstation. In some embodiments, at least one output manifold is configured to direct at least some negatively ionized air at one or more angles divergent from the barrier.

In some embodiments, the system further includes at least one light source configured to illuminate at least part of an area subtended by the barrier when the system is activated or when the system is active and the illuminated subtended area is readily-discernable by a viewer.

In some embodiments, the system is configured with a mounting system including at least a first attachment point to enable the system to be integrated with, or installed in, on, or proximate to, a stroller, infant or child seat or carrier, baby carrier, crib, playpen, a passenger vehicle, or a transportation device. In some embodiments, the first attachment point is configured to be removably attached to and mechanically supported by a first adapter. In some embodiments, at least one of removing the system from or mounting the system to the first adapter does not require tools or does not require modifications to the first attachment point of the system. In some embodiments, the first adapter is attached to a first object, at least a second adapter is attached to a second object, and the system is configured to be removed from the first adapter and mounted on the second adapter. In some embodiments, the system further includes a control system and at least one fan, wherein the control system is programmed to alter the state of the speed of the at least one fan to prescribed speeds according to the detection of movement of the system, movement of the system, of the presence or non-presence of a person or an object at least one prescribed location, of prescribed sounds or sound pressure levels originating from at least one prescribed location or direction relative to the system, ambient light levels, or the dimensions or geometry of the area downstream of the at least one manifold. In some embodiments, the system is configured such that the output manifold can be adjusted or reconfigured to direct at least some negatively ionized air towards an occupant of the stroller, infant or child seat or carrier, baby carrier, crib, playpen, a passenger vehicle, a transportation device.

In some embodiments, the system is configured such that the manifold is adjustable or such that the manifold can be rotated about an axis approximately perpendicular to the direction of airflow or such that the manifold can be rotated about an axis approximately parallel to the direction of airflow. In some embodiments, the system further includes at least one grounding conductor, wherein the at least one grounding conductor is electrically connected to a negative input voltage reference, a negative battery terminal, or the ground reference of the negative voltage source.

BRIEF DESCRIPTION OF DRAWINGS

Non-limiting and non-exhaustive embodiments of this disclosure are described with reference to the following figures, wherein like reference numerals refer to like parts throughout the various views unless otherwise specified.

DETAILED DESCRIPTION

Figure 1:
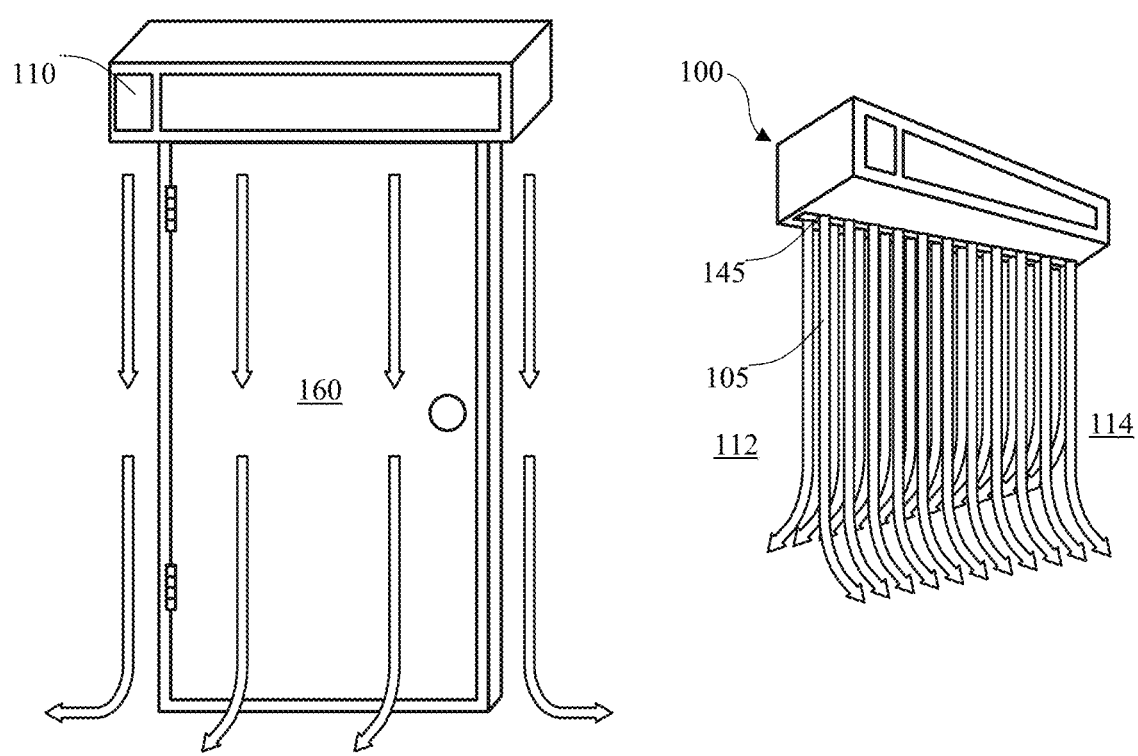
FIG. 1 depicts a germicidal partition system in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques, and implementations of the present disclosure to those skilled in the art. Embodiments may be practiced as methods, systems, or devices. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Acronyms Used
    AC—Alternating current
    AI—Artificial intelligence
    CDC—Centers for Disease Control and Prevention (US Government Agency)
    COVID-19—Coronavirus 2019 (SARS-CoV-2)
    DC—Direct current
    HVAC—Heating, ventilation, and air conditioning
    HV PSU—High voltage power supply unit
    LED—Light-emitting diode
    ML—Machine Learning
    N95—Particulate respirator meeting the N95 NIOSH air filtration rating
    NAI—Negative air ions
    PPA—Personal protection augmentation
    PPE—Personal protective equipment
    PPM—Parts per million
    UV—Ultraviolet (light, wavelength ≤400 nm)

Embodiments

Some embodiments of the present invention are directed to a system configured to create a laminar curtain of negatively ionized air across a doorway or portal. An air ionizer uses high-voltage electricity to ionize air molecules. Ionizing air molecules comprises imparting either a positive or a negative charge to air molecules. The ionized air molecules, herein referred to as ions, tend to attract other airborne particles, including viruses and bacteria, and transfer their charge to said particles. Ionized air has been shown to inactivate virus particles and bacteria. Additionally, ionized particles tend to be attracted to earth ground (in the electrical sense). Such attraction causes ionized particles to precipitate out of the air and onto the floor or other surfaces, as well as intentionally grounded or charged plates. Whether or not such individual microbe particles are inactivated, they cease to be airborne, reducing the likelihood of person-to-person transmission.

Multiple studies have shown that air ionizers are effective at reducing the spread of airborne contagions and preventing the spread of the influenza virus between lab animals held in close proximity. In countries previously affected by the SARS virus (a strain of coronavirus), manufacturers have added ionizers to many consumer products, including household appliances.

Properly designed air ionizers do not produce harmful byproducts, require no consumables, are energy-efficient, and can be scaled up or down to suit a wide range of applications. Because ionized air does not cause any known negative effects to humans, it is considered safe for ionizers to be active in close proximity to people.

Air ionizers function by passing air through one or more electrodes held at high (positive or negative) voltage—typically on the order of at least several kilovolts. Air molecules passing near the electrodes pick up a charge—they are ionized. Because their charge is the same polarity as the electrode(s), the ions are repelled away from the electrodes. As a result, some ionizers do not use a fan to create airflow—the ions themselves cause positive airflow out and away from the ionizer. Other ionizers may use fans to enhance airflow or direct the airflow in a particular direction; typically, net air ion production (e.g., ions per second) increases with air velocity over the electrodes.

In the present context, air ionizers are able to continuously neutralize and precipitate aerosolized, airborne virus particles out of the air independent of ventilation. Strategically placed ionizers can effectively isolate rooms with respect to airborne pathogens from hallways and other rooms without physical barriers. This may be of particular interest in medical facilities wherein patients may be separated only by vertical partitions, such as curtains.

In some embodiments, the laminar curtain may work similar to existing air curtains, with the addition of an anode system configured to create a negatively ionized air stream. An example of such an embodiment is shown in FIG. 1. Embodiments create a protection from airborne pathogens, dust, smoke, or other airborne matter that is susceptible to ionization. When installed above a doorway, the system may be configured to create a downward flow of ionized air, forming a virtual partition between areas.

In some embodiments, a high concentration of NAI is maintained for a significant distance within the laminar output. For example, in some embodiments, the NAI concentration four feet from the manifold may be over 1 million ions per cubic centimeter of air. For example, in some embodiments, the NAI concentration directly out of the manifold may be over 40 million or 50 million ions per cubic centimeter of air.

Returning to FIG. 1, a horizontal laminar curtain of negatively ionized air 105 is discharged from the bottom of the partition system 100 and directed downward. In some embodiments, the system is configured to discharge a horizontal laminar curtain of negatively ionized air 105 from the top of the partition system 100 and directed upward. In some embodiments, the system is configured to discharge a vertical laminar curtain of negatively ionized air (not shown) from one side to another side of a portal, perpendicular to the direction shown in FIG. 1. Some embodiments of the system 100 may include a laminarizer or output manifold 145.

In some embodiments, in anion-only generation mode, the ozone production of the partition system 100 may be between zero and 0.01 PPM. In some embodiments, increasing anode potential with respect to ground or changing the geometry or positioning of components proximate to the anodes (not shown) within the partition system 100 may cause predictable concentrations of ozone to be produced. In some embodiments, such mechanism or circuitry may be used by the system 100, via its control system 110, to inhibit, enable, or regulate the production of ozone.

In some embodiments, the manifold 145 is designed such that the airflow exiting the manifold 145 is laminar and of a prescribed geometry. For example, the airflow exiting the manifold 145 may have a net cross-sectional shape of at least one of a polygon, circle, ellipse, or oval. In some embodiments, this geometry is designed such that the laminar curtain of negatively ionized air 105 is at least as wide as the door 160 over which the system is affixed and extends downward for at least four feet. In some embodiments, the laminar curtain of negatively ionized air 105 is configured to reduce at least one of the transfer of contaminants or the concentration of viable contagions between a first air mass 112 and a second air mass 114. In some embodiments, the term contaminant may also include contagions and contagions may also refer to contaminants. Contagions and contaminants may be polluting substances that render an environment less safe or impure, and may comprise bacteria, viruses, fungi, dust, particles, poisons, pesticides, and drugs.

In some embodiments, it is possible to adjust the angle of the manifold 145 with respect to the system 100 to control the direction of airflow. In some embodiments, the width of the air 105 exiting the manifold 145 may be adjustable to cover a wider or smaller area. In some embodiments, the manifold 145 can be reconfigured or adjusted electromechanically, manually, and/or by the installation of one or more accessories, such that the otherwise laminar air 105 output of the system is diffused or diffuse. In some embodiments, this manifold configuration may be used to facilitate more effective mixing of anions with room air during non-partition operations or time periods.

Figure 2:
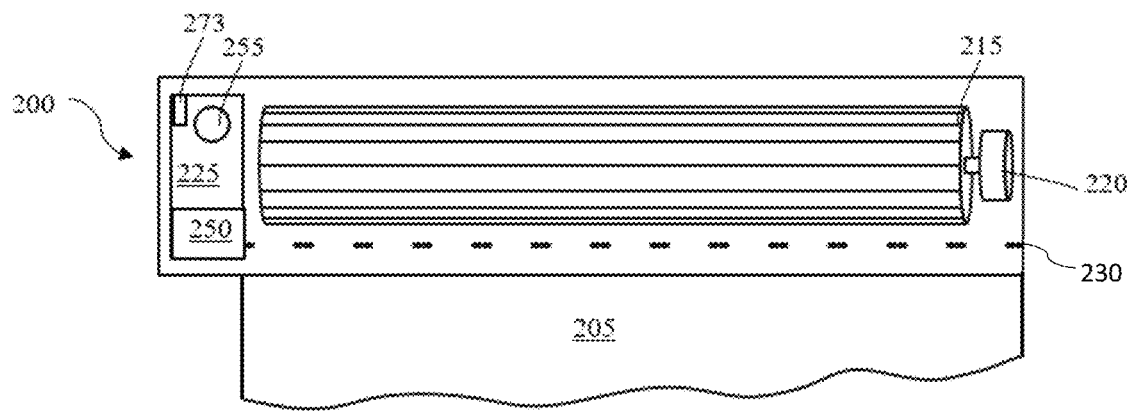
FIG. 2 depicts a germicidal partition system having a squirrel cage fan, motor, and high voltage power supply unit in accordance with one embodiment.
Figure 8:
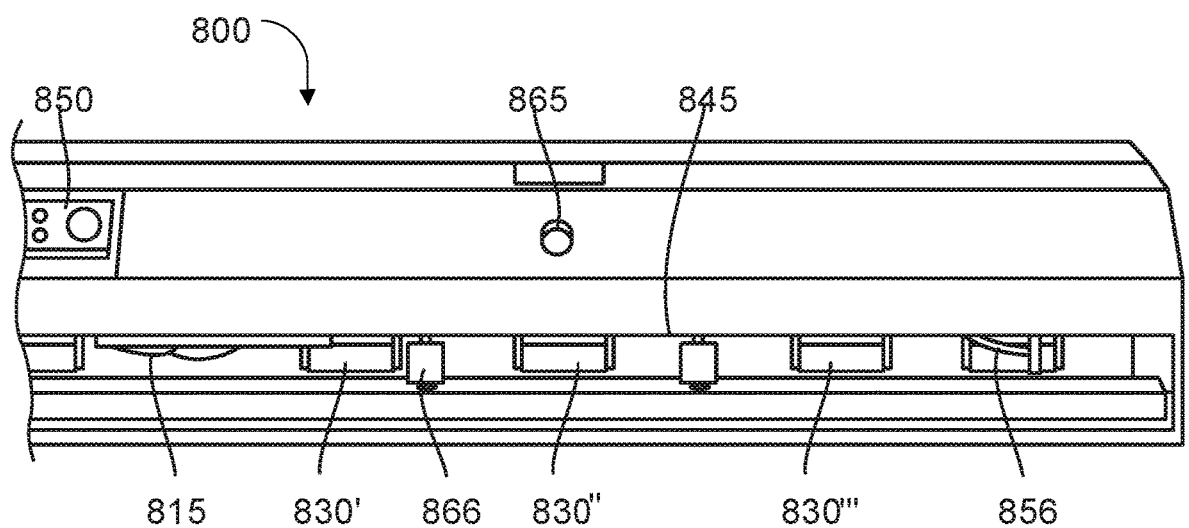
FIG. 8 depicts a bottom view of a germicidal partition system with anodes in accordance with one embodiment.

FIG. 2 illustrates an embodiment of a germicidal partition system 200 having a squirrel cage fan (also known as a tangential fan) 215, motor 220, and a power source 225, such as a high voltage power supply unit or other negative high-voltage source, in accordance with one embodiment. In some embodiments, the system 200 may include a line of anodes 230 below the squirrel cage fan 215 and may blow air around, over, or past the anodes 230 to create a curtain of negatively ionized air 205. Anodes, as referred to herein, are electrodes held at a large negative potential. The anodes 230, combined with the power source 225 and at least one high voltage conductor (e.g., such as the one shown in FIG. 8), comprise a negative ion generator, sometimes referred to as an ionizer.

Some embodiments of the system 200 may include an output manifold or laminarizer (shown in FIG. 1). In some embodiments, a fan 215, powered by a fan motor 220, draws air through the system 200, with said air exiting through the manifold. In some embodiments, the anodes 230 impart negative charge to air flowing through the system 200 and air exiting the system 200 in the curtain of negatively ionized air 205 contains a prescribed concentration of anions. For example, in some embodiments, the air outputted through the manifold in the curtain of negatively ionized air 205 comprises at least 40 million negative air ions per cubic centimeter of air. In some embodiments, the air outputted through the manifold in the curtain of negatively ionized air 205 comprises at least 20 million negative air ions per cubic centimeter of air. In some embodiments, the air outputted through the manifold in the curtain of negatively ionized air 205 comprises at least 1 million negative air ions per cubic centimeter of air.

In some embodiments, the motor 220 may be an electric motor such as a universal motor, brushless DC motor, or an induction motor. Electric motors harness electromagnetism to generate motion. The motor 220 is coupled to the fan 215 in some embodiments. In some embodiments, the torque produced by the motor 220 is transferred to the fan 215, causing rotation.

In some embodiments, the negative ion generator and the fan 215 are powered by the at least one power source 225 and controlled by the control system 250. In some embodiments, the power source 225 may be a battery and charger system or may be a plug-in power supply. In some embodiments, the system 200 may be battery powered or may use mains electricity. In some embodiments, mains electricity may simplify and reduce the cost of the negative ion generator. Some embodiments may use modular HV PSU's (one for DC or battery and one for mains) or may use a hybrid system optimized for both battery and mains. In some embodiments where both a battery and mains power sources 225 are present, the system 200 is able to automatically switch to using the battery power source 225 in the event of a blackout or loss of mains power. Some embodiments may have mode flexibility, such as passive quiescent ion generation, constant or periodic fan activation. In some embodiments, the system 200 may be permanently integrated into a building and hard-wired into a building or facility's electrical system.

In some embodiments, the power source 225 is at least one primary or rechargeable battery contained within or attachable to the housing. In some embodiments, the system 200 may further comprise a mechanism whereby an installed battery can be charged while the system 200 is connected to mains power. In some embodiments, the power source 225 is external to the system and is connected to the device by a plurality of conductors (e.g., a cable). In some embodiments, the power source 225 is an AC-to-DC converter.

The design and construction of the high, negative voltage power supplies for negative ion generators ("negative ion generator power supplies") varies significantly depending on the power source. In some embodiments, mains-AC-powered negative ion generator power supplies may use a variant of a Cockcroft-Walton voltage multiplier circuit (comprising primarily diodes and capacitors). In some embodiments, negative ion generators powered by lower-voltage DC sources, such as batteries, may employ switch-mode inverters that use high-voltage step-up transformers. In some embodiments, the system 200 may use a USB-C power supply.

Some embodiments comprise a low-voltage (less than 48 V) DC-powered negative ion generator power supply as the power source 225. In some embodiments, when operating from a battery power source, the DC battery powers the negative ion generator power supply directly. In some embodiments, when operating from a mains AC power source, an AC-to-DC converter is used to convert and step down the mains voltage to the DC supply voltage required by the DC-powered negative ion generator power supply.

Some embodiments comprise a mains-AC-powered negative ion generator power supply as the power source 225. In some embodiments, when operating from a mains AC power source, the negative ion generator power supply is powered directly from the mains. In some embodiments, when operating from a battery power source, a DC-to-AC inverter is used to convert and step up the battery voltage to mains AC voltage and frequency and the negative ion generator power supply is powered by said inverter. While the DC-to-AC inverter does contain a step-up transformer, said transformer is usually of simpler, more economical construction than the high-voltage step-up transformer typically used in DC-only negative ion generator power supplies. In some embodiments, the resulting negative ion generator power supply is simpler, smaller, and more economical than two separate negative ion generator power supplies while affording the flexibility to run on battery or mains AC within the same unit.

Some embodiments comprise a first low-voltage DC-powered negative ion generator power supply and a second mains-AC-powered negative ion generator power supply as the power source 225. In some embodiments, when operating from a battery power source, the first negative ion generator power supply is used. In some embodiments, when operating from mains AC, the second negative ion generator power supply is used. In some embodiments, the negative ion generator power supply is a modular, separable component of the device, allowing one of the first or second negative ion generator power supplies to be fitted to the unit for battery or mains power source operation, respectively. Some embodiments may exclusively use a battery power source.

In some embodiments where a power source 225 is one or more batteries, the device further comprises one or more annunciators 255. In some embodiments, the annunciator(s) 255 activate when a power source 225 level falls below a certain threshold and may indicate the approximate number of disinfection cycles remaining for the given level of the power source 225. In some embodiments, an annunciator 255 is audible, comprising, e.g., a buzzer, beeper, speaker, etc. In some embodiments, an annunciator 255 is visual, comprising, e.g., a lamp, light, blinking indicator, etc. In some embodiments where the control system 250 is able to communicate with other digital or electromechanical systems, annunciation may be by means of message(s) or electrical signal(s) sent to or exchanged with one or more external systems.

In some embodiments, the control system 250 may use sensor data to adjust fan speed, ionizer power, or other parameters based on, for example, relative humidity, air temperature, detected contaminant levels, or the user's movement. In some embodiments, the control system 250 is electromechanical, digital, or a combination of electromechanical and digital.

In some embodiments, the control system 250 responds to a motion activation or audio triggering event by activating the fan 215 and the negative ion generator for a prescribed period of time. In some embodiments, the duration of activation may be extended if the control system 250 detects continued motion or the proximity of a person or persons within a prescribed area, or due to other conditions detected by the sensors. In some embodiments, the duration of activation may be extended if the control system 250 detects that a door or other portal remains open, either partially or fully. In some embodiments, the duration of activation may be further extended depending on how long the door or other portal remains open or how many times the door was opened and closed during the present activation period. In some embodiments, after the prescribed or extended period of time elapses, the control system 250 deactivates the fan 215 and negative ion generator.

In some embodiments, upon motion activation or audio triggering, the fan 215 may run at a higher-than-typical speed for a short period of time. For example, the short period of time may be five seconds, ten seconds, thirty seconds, one minute, or two minutes. In some embodiments, the higher speed may provide a positive audible indication to the user that the device is active and may help ensure that any dust or debris that may have collected on the device while it was idle is cleared out before the user passes through the curtain of negatively ionized air 205. In some embodiments, after this initial period, the fan speed may reduce to a prescribed or configurable speed to minimize fan and airflow noise while providing a prescribed level of germicidal partition protection. In some embodiments, acoustic noise produced by the system 200 during operation is less than 55 dBA.

In some embodiments, the system 200 may comprise switches, buttons, or other mechanisms 273 to allow the user to turn the curtain of negatively ionized air 205 on and off, adjust the fan speed, check the battery charge level, or perform other operations.

In some embodiments, the system 200 can be configured or operated in a mode wherein the negative ion generator is energized while the fan 215 is turned off. In some embodiments, airflow through the system 200 is induced electrostatically by the negative ion generator, providing a continuous, low-velocity flow of ionized air when the fan 215 is turned off after the air passes over the anodes 230. When air molecules or other particles become negatively charged, they are repelled from the one or more anodes 230, which are also at a negative potential. Effectively, air is electrostatically "pumped" through the system 200.

In some embodiments, the system 200 can be configured to operate periodically or continuously to provide ongoing air quality improvement and germicidal action in an area.

In some embodiments, the system 200 varies the concentration of anions injected into the negatively ionized air 205 via its control system 250. In some embodiments, the anion concentration variation is controlled by adjusting at least one of the input or output voltage of the power source 225, e.g., through pulse-width modulation or pulse-density modulation of the negative ion generator's input voltage.

In some embodiments, at least one parameter comprising the anion concentration, anode voltage, fan speed, and/or device activation duration may be adjusted as a function of parameters including, but not limited to, air temperature, relative or absolute humidity, barometric pressure, or air quality index (measured locally or communicated to the device via one or more communications modules). In some embodiments, the system 200 may adjust any of the parameters based on the presence of infections in persons known to be proximate to the system 200, local outbreaks of airborne infectious diseases, and/or configuration.

Figure 3:
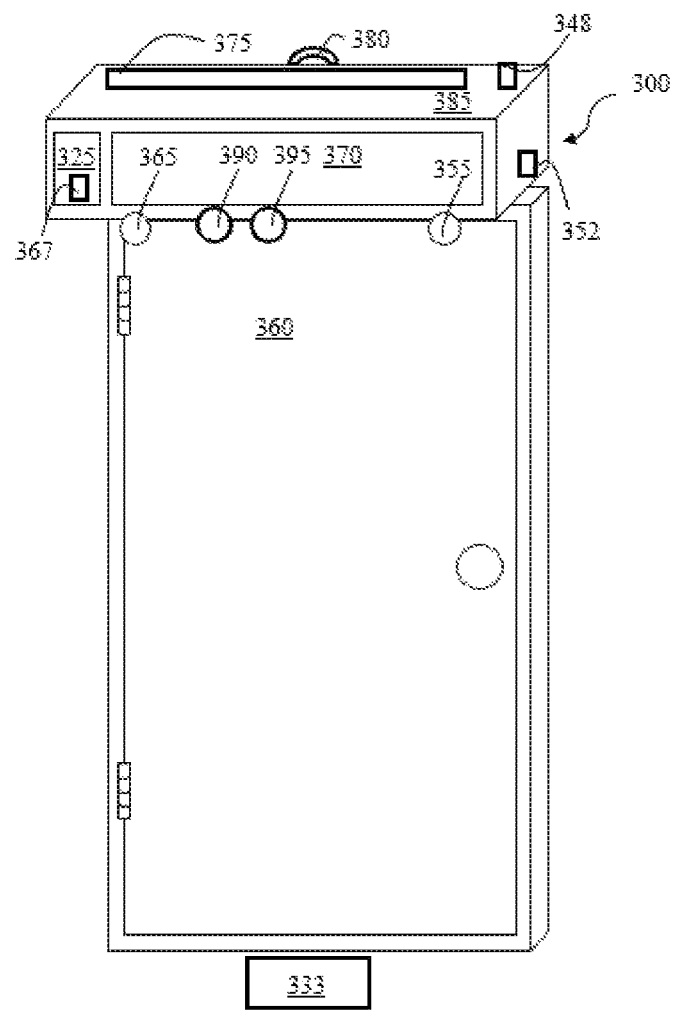
FIG. 3 depicts a germicidal partition system secured above a portal in accordance with one embodiment.

FIG. 3 depicts an embodiment of a germicidal partition system 300 secured above a portal 360 in accordance with one embodiment. A portal 360 may refer to a door, doorway, opening, or other equivalent recognized by a person having ordinary skill in the art. In some embodiments, the air curtain may be outputted behind or in front of a portal 360. In some embodiments, the air curtain may replace a solid portal 360, such as a door, completely.

In some embodiments, the system 300 may comprise at least one of a motion sensor 365, a control panel 325, at least one annunciator 355, a user interface 370, and an intake 375.

In some embodiments, the intake 375 may be a front intake (not shown). In some embodiments, the intake 375 may be a top intake 375. In some embodiments, the intake 375 may be a bottom intake (not shown).

The at least one motion sensor 365 may be pyroelectric (or passive) infrared sensors in some embodiments. In some embodiments, the width of the germicidal partition system 300 may be between 30 and 36 inches. In some embodiments, the height of the germicidal partition system 300 may be between 4 and 6 inches. In some embodiments, the depth or projection of the germicidal partition system 300 may be between 4 and 8 inches.

In some embodiments, users may mount the system 300 with at least one mounting system 380. Mounting may include hanging, suspending, directly affixing, or other means of permanently or temporarily coupling the system to another object. In some embodiments, the mounting system 380 may comprise a simple, no-tools-required system such as a non-permanent adhesive on at least one side of the unit. In some embodiments, the mounting system 380 may include a screw system wherein the system screws into above-door framing. In some embodiments, the system 300 may hang from screws and/or studs or is configured to attach to mounting bracket. In some embodiments, the mounting system 380 may include L-brackets or another attachment system for transom windows.

In some embodiments, a mounting system 380 comprises the hook or loop side of a hook-and-loop attachment system. In some embodiments, a mounting system 380 comprises one or more adhesive strips or sheets that adhere the device to a wall, transom window, door frame, or other surface proximate to the portal. In some embodiments, a mounting system 380 comprises a plurality of holes, slots, hooks, grooves, or other features in the device housing which engage with a corresponding plurality of mating protrusions, such as nails, screws, hooks, brackets, etc. affixed to mounting points on a wall, door frame, or other surface proximate to the portal. In some embodiments, retention of the system 300 relies on the force of gravity to maintain engagement between the corresponding features of the system housing 385 and the mating protrusions. In some embodiments, a mounting system 380 comprises one or more magnets, with the external mounting point being a ferrous/magnetic material, such as steel or iron.

In some embodiments, a mounting system 380 further comprises one or more elastomeric, rubber, foam, or other compliant or spring elements to dampen vibrations and/or reduce mechanical coupling of vibrations from the system 380 into the mounting surface. In some embodiments, the user may use the control panel 325 to adjust fan speed in the system 300 to avoid or mitigate vibration or vibration coupling between the device and the mounting point(s)) due to resonance(s).

In some embodiments, a mounting system 380 further comprises an external component. In some embodiments, the external component and part of the system 300 are designed such that they mate together, providing retention of the system 300 in or by the external component; the external component is mechanically attached to a mounting point proximate to the portal 360. In some embodiments, the external component contains or can be fitted with one or more strain reliefs for electrical wiring for permanent, hard-wired installations.

In some embodiments, the germicidal partition system 300 may couple to existing forced air supplies, such as HVAC vents, HVAC units, portable fans, or existing air purifiers. In some embodiments, the mounting system 380 may include a plenum for air intake, such that the fan intake is not blocked by the wall, portal 360, or other surface. In some embodiments, the mounting system 380 may include an accessory configured to allow the germicidal partition system 300 to be temporarily attached to a pole or rod, such as is found in tents and temporary shelters, via an adjustable clamp mechanism.

Some embodiments may be installed horizontally, across the top of a portal opening, and air may be expelled from top to bottom of the portal 360. In some embodiments, the system 300 may be installed to output a vertical air curtain on one or both sides of the portal 360. Horizontal installation integrated on the floor may be the most effective in thermodynamic terms but in some embodiments but may be problematic where public pedestrian traffic crosses the doorway.

In some embodiments, the mounting system 380 facilitates installation of the system 300 on a ceiling or other overhead surface with the top of the device parallel and proximate to or in contact with the ceiling or other overhead surface. In some embodiments, the mounting system 380 facilitates suspension of the system from a ceiling or other overhead surface. Some embodiments may be deployed or installed to leverage the system's capabilities away from or absent a portal 360. For example, in some embodiments, a system 300 may be installed in a hallway, at the junction of hallways, or as an invisible room partition, such as between beds in a medical ward or between tellers and customers in a bank.

In some embodiments, the system 300 further comprises at least one motion sensor 390 to detect motion or movement proximate to the system 300. Common examples of motion sensors 390 include, non-exhaustively, active or passive infrared sensors, RADAR, time-of-flight sensors, imaging sensors, digital cameras, ultrasonic sensors, proximity sensors, electro-optical, magnetic, inductive, capacitive, or audio/sound sensors. In some embodiments, motion sensor data is fed to and/or read by the control system.

In some embodiments, motion sensor data is used by the control system to trigger activation of the device according to prescribed or configurable parameters ("motion activation"). In some embodiments, the parameters may include, but are not limited to, motion sensor sensitivity, motion sensor range, fan speed, negative ion generator power level, and the duration of activation. In some embodiments, the control system will trigger device activation in response to sensor data indicative of a person or persons approaching the portal. Motion activation may apply to motion on the device-side of the portal and may also apply to motion on the opposite side of the portal. For example, motion activation may apply to a person approaching an open door or a portal without a door).

In some embodiments, the control system may trigger device activation in response to sensor data indicative of the portal 360 opening or beginning to open. In some embodiments, such a door or portal-opening motion activation capability does not require modifications to the door, door frame, or other surrounding features of a portal 360.

In some embodiments, the system 300 further comprises at least one audio sensor 395. In some embodiments, the at least one audio sensor 395 may be a microphone. In some embodiments, the control system is able to use audio sensor data to trigger device activation based on prescribed, configurable, programmable, and/or learned sound/audible indications ("audio triggering"). In some embodiments, audio triggering may be performed in response to detection of a doorbell, door chime, door knocker, or other knocking on the door. In some embodiments, audio triggering may be performed in response to detection of the sound of a key being inserted into a lock, actuation of a lock, turning of a door handle, etc.

In some embodiments where the system 300 comprises at least one audio sensor 395, the system 300 may provide a means for the user to disable or disconnect all audio sensors 395 from the control system with the control panel 325. In some embodiments, a user may disable or connect an audio sensor 395 for reasons of privacy, policy, or other restrictions. In some embodiments, the system 300 further comprises one or more visual indicators or annunciators 355 that indicate when the audio sensors 395 are enabled. In some embodiments, the means of positive disablement of audio sensors 395 is an electromechanical switch 367 that disconnects the audio sensors 395 from the control system, disconnects power from the audio sensors 395, or equivalent.

In some embodiments where the system 300 comprises at least one motion sensor 365 or audio sensor 395, the control system may use at least one of adaptive or intelligent algorithms, such as AI or ML to refine the set of conditions that should trigger system activation or that should not trigger system activation. Said algorithms may also consider other data available to the control system, such as time-of-day, ambient lighting, the states of other devices with which it is able to communicate and user preferences. In some embodiments, the system 300 may not activate or trigger due to the movement of pets or small children proximate to a portal 360. In some embodiments, the system 300 may distinguish between the sound of the owner's actual doorbell and the sound of a doorbell on a television or other recorded program, a neighbor's doorbell, etc.

The system 300 may include a controller and some form of user interface, such as a control panel 325 to allow the user to control power, adjust parameters such as fan speed, and set the system 300 to run for a fixed or customizable time duration.

In some embodiments, the control system is able to detect with at least one sensor 365, 395 or communication with other devices that the fan(s) of a forced-air heating or cooling system are active. In some embodiments, upon such detection, the control system may activate the negative ion generator and fan within the system 300 such that the negatively ionized air is able to circulate and mix more effectively over a larger area/volume due to the increased air circulation due to the forced-air system. In some embodiments, the system 300 may remain running for a prescribed or configurable period of time or it may automatically deactivate when it detects that the forced-air system's fans have turned off.

In some embodiments where the system 300 comprises one or more controls on the control panel 325 or otherwise, one or more controls may include magnetic switches, magnetic sensors, magnetometers, reed relays, inductive sensors, or any equivalent recognized by a person having ordinary skill in the art ("magnetic controls"). In some embodiments, a user may actuate the one or more magnetic controls using a permanent magnet, electromagnet, iron, steel, or other mass of magnetic or ferromagnetic material attached to, installed in or on, embedded in, or integral to a rod, pole, stick, or equivalent. In some embodiments, the user's height does not limit the user's ability to actuate the device's controls which, due to the height of the portal 360, may otherwise be beyond the user's reach. In some embodiments, the method of actuation avoids direct contact with the system 300 and, thus, the spread of pathogens by surface contact.

Some embodiments may have different control mechanisms and user interfaces. In some embodiments, the system 300 could be configured such that the control panel 325 is on the left side and some such that the control panel 325 is on the right side. In some embodiments, the system 300 may be configured such that the control panel 325 is accessible for those with a disability. In some embodiments, the control panel 325 may be visible at all times. In some embodiments, the control panel 325 may be hidden from view. In some embodiments, control may be wireless or integrated into a smart home.

Some embodiments incorporate one or more interlocks 352, such as electro-mechanical switches, that disable or deenergize at least one of the negative ion generator power supply, fan motor, or other components if the housing 385 is opened or disassembled or certain removable parts of the housing 385 are not fitted or installed.

In some embodiments, the control panel 325 comprises one or means of temporarily disabling or locking the controls to prevent inadvertent adjustments. In some embodiments, one or more of the controls is designed to be "child-proof", "child-resistant", "child-safe", or any equivalent thereof. In some embodiments, the control is difficult or impossible for a baby or child to actuate. In some embodiments, the controls are locked or unlocked by actuating multiple controls simultaneously or by maintaining actuation of one or more controls for a prescribed time duration.

In some embodiments, the system 300 comprises one or more communications modules 348 permitting the system 300 to be wirelessly monitored and/or controlled from or with an external device. In some embodiments, a communications module 348 communicates via at least one of BLUETOOTH, WIFI (IEEE 802.11) wireless networking, a mobile or cellular network (e.g., GSM, LTE, 5G, etc.), power line networking (a data network superimposed on a buildings mains supply wiring), or an equivalent recognized by a person having ordinary skill in the art. In some embodiments, a communications module 348 communicates with or permits integration with other wireless products, such as baby monitors, home security systems, home monitoring systems, etc. or sensors, such as video cameras, surveillance equipment, etc.

In some embodiments, the control system, via a communications module 348, is able to communicate with home automation systems, smart home systems or devices, networked security systems, etc. In some embodiments, the system 300 can be controlled, monitored, triggered, or inhibited from triggering, and/or configured via one or more of said systems and/or may integrate with one or more of said systems. For example, in some embodiments, the system 300 could be configured to run when informed by a "smart" thermostat that a forced-air fan system is active. In some embodiments, the forced-air fan system is a proximate forced-air fan system.

In some embodiments, the control system of a first system 300 is able to communicate with the control system of another device. In some embodiments, such communication may be peer-to-peer between the system 300 and another device or may be facilitated or governed by another system that communicates with the system 300 and the device. In some embodiments, the activation of the device may be triggered or influenced by the activation or non-activation of the system 300. For example, in some embodiments, if a person walks past the system 300 in a direction that is likely to lead the person to another device, the other device may activate early, in anticipation of the person's arrival, to pre-disinfect the area.

In some embodiments, the system 300 may be located above a door or other portal 360 to a room or area known to contain contagious individuals. In some embodiments, the act of opening this portal 360 may trigger a second device—providing protection for a nearby room or area—to further-inhibit the transfer of airborne pathogens between the respective areas. In some embodiments, coordination between the system 300 and another device may comprise intelligent, adaptive, and/or learning algorithms, such as those of artificial intelligence, machine learning, deterministic algorithms, control theory, or heuristics. In some embodiments, such coordination may use as inputs contemporaneous or historical sensor data from at least one of the system 300 or other device, sensor or other data from external sources, user input, or configuration.

In some embodiments, the germicidal partition system 300 may include an efficiently grounded plate 333 held at an electrical potential opposite from that of the system's output or at ground potential with respect to the system. In some embodiments, the plate 333 may attract and retain pathogen particles or other airborne contaminants in the environment and may be used to assay pathogen or contaminant presence and/or concentration in an area. In some embodiments, the plate 333 may be within the housing 385. In some embodiments, the plate 333 may be external to the system 300 and may be, for example, an electrostatically dissipative or electrically conductive floor title. In some embodiments, the plate 333 may be covered by a rug or mat, such that the rug or mat can be removed and cleaned to remove pathogen particles. In some embodiments, the plate 300 may be wiped down with cleaner or water to remove pathogen particles.

Figure 4:
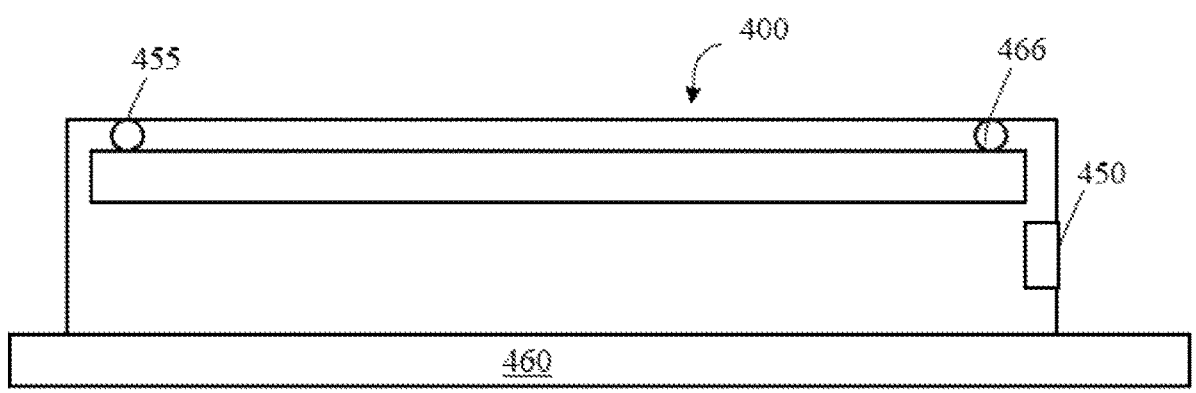
FIG. 4 depicts a bottom view of a germicidal partition system in accordance with one embodiment.

FIG. 4 depicts a bottom view of an embodiment of a germicidal partition system 400 in accordance with one embodiment. In some embodiments, the system 400 further comprises one or more visual annunciators 455, such as indicator lights, light-emitting diodes (LEDs), etc. In some embodiments, a visual annunciator 455 may be used to indicate at least one of the system's 400 power status (on, off, standby, etc.), mode, or battery capacity.

In some embodiments, the system 455 further comprises one or more light sources 466, such as white LEDs, that provide convenience lighting at or near the portal 460. In some embodiments, the light sources 466 are controlled by the control system 450 and may be activated in concert with or independent of the negative ion generator and/or fan.

In some embodiments, the system 400 may use convenience down-lighting. In some embodiments, the system 400 may be integrated into a smart home system, such as running the ionizer and fan when home HVAC fan is running, unit starts up when someone approaches the door or as user drives up to dwelling, adjust duty cycle based on local air quality index, etc.

Figure 5:
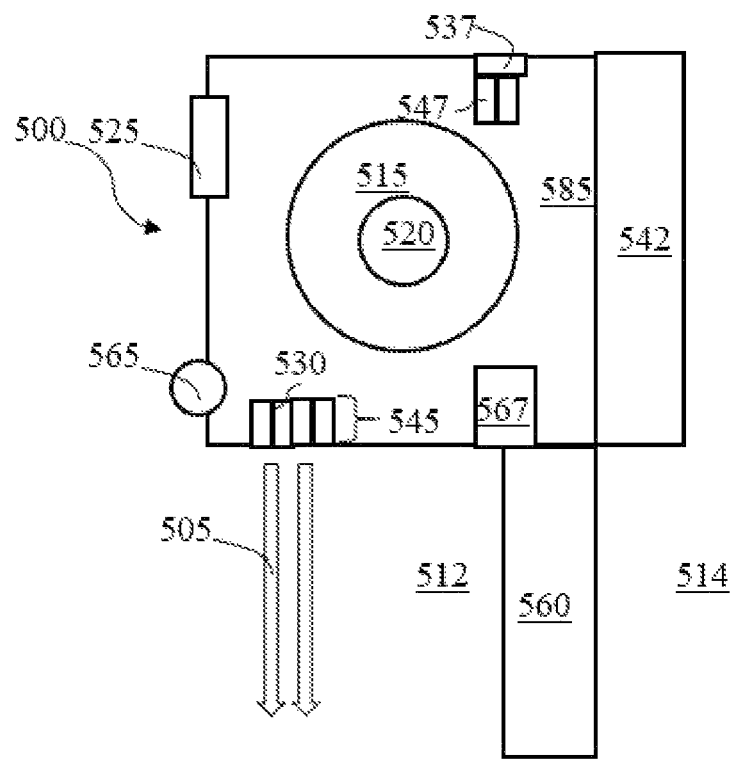
FIG. 5 depicts a side view of a germicidal partition system in accordance with one embodiment.

FIG. 5 depicts a side view of an embodiment of a germicidal partition system 500 mounted on a wall 542 above a portal 560 in accordance with one embodiment. In some embodiments, the germicidal partition system 500 may use a fan 515 and a motor 520 inside a housing 585, connected to a laminarizer or manifold 545, to output a laminar air curtain 505. In some embodiments, the germicidal partition system 500 includes at least one anode 530, such that the germicidal partition system 500 is configured to output a laminar air curtain 505 with a prescribed concentration of negative air ions.

Some embodiments may use a fan 515 to propel and circulate the negative ions. In some embodiments, the fan 515 may run for a certain number of seconds after a motion sensor or other trigger 565 is activated. In some embodiments, the fan 515 may run periodically using a configurative or adaptive control. In some embodiments, the fan 515 may be user-configurable and may run continuously. In some embodiments, the fan 515 may be a multi-speed fan. In some embodiments, the fan speed may be adaptive, may have a learning mode, and/or may be user configurable. In some embodiments, the fan 515 may have a passive mode, comprising at least one of the fan 515 being off and/or electrostatic self-pumping. In some embodiments, the fan 515 may be direct or belt driven. In some embodiments, the fan 515 may use at least one of centrifugal, axial and crossflow to propel air through an ionizer and out through the manifold 545. In some embodiments, the manifold 545 may be adjustable to increase the performance of the outputted air curtain 505 according to each situation.

Some embodiments may be non-recirculating germicidal partition systems 500. Some embodiments may be recirculating. A non-recirculating system 500 may be configured to discharge the air to the environment. A recirculating system 500 may be configured to collect and return the air from the discharged air. Recirculating air curtains may be more energy efficient in some embodiments.

In some embodiments, the housing 585 and manifold 545 are designed such that internal energized or moving parts cannot be accessed or touched from outside the device. In some embodiments, the openings in at least one of the manifold 545 or air intake 537 are typically small enough to prevent insertion of a body part.

In some embodiments, the system 500 further comprises one or more adjustable/repositionable components. In some embodiments, these components may be part of the manifold 545 or may be separate, substantially independent parts of the manifold 545. In some embodiments, changing the position of the one or more adjustable/repositionable components, possibly in conjunction with adjusting anode potential, inhibits ozone production or controls the production of ozone. In some embodiments, the system 500 is capable of producing germicidal/antimicrobial concentrations of ozone. In some embodiments, the one or more adjustable/repositionable components are actuated electromechanically under the control of and pursuant to the programming or configuration of the system's control system. In some embodiments, the system 500 further comprises a mechanism 525 or circuitry that enables adjustment of the one or more adjustable and/or repositionable components' potential and/or impedance with respect to electrical/earth ground.

In some embodiments, one or more anodes 530 are embedded in the structure of the manifold 545. For example, in some embodiments, the manifold 545 or manifold may be injection molded, 3D-printed, thermoset, etc. such that the one or more anodes 530 are retained or partially contained within the structure of the manifold 545.

When air is passed over the anodes 530, some fraction of the air molecules themselves and other airborne particles acquire a negative electrical charge; such negatively charged molecules or particles are referred to as anions and the resulting air mass is referred to as negatively ionized air. First, charges transferred to microbes (from the anodes or from charged air molecules) cause damage to the microbes and kill or deactivate the microbes—rendering them essentially harmless to humans. Anion-rich air also tends to cause other air contaminants, such as pollen, dust, allergens, smoke, and odor molecules, to precipitate out of suspension—again, improving air quality. Some embodiments described herein produce a laminar flow of negatively ionized air 505 downward across doorways or portals 560. In some embodiments, the airflow itself reduces air exchange across the portal and the anions' germicidal effects reduce the concentration of live and/or active microbe aerosols that do cross the portal 560. In addition, anions may be injected into the spaces on both sides 512, 514 of the portal 560, providing further germicidal and air-purifying benefits in some embodiments.

In some embodiments, the system 500 may further comprise one or more air filtration components 547 within the intake 537, in the housing 585, or external to the housing 585. In some embodiments, the system's air intake 537 is fed, in whole or in part, by an external air filtration, air treatment, germicidal treatment, or other purification or disinfection system. In some embodiments, the system 500 may further comprise one or more other germicidal or antimicrobial air treatment components, such as treating air passing through the device with germicidal ultraviolet irradiation.

In some embodiments, the air entering through an inlet grille as the intake 537, sometimes with filter functions 547 and sometimes without filter functions 547, is compressed by at least one internal fan 515 and forced though an air outlet (shown as manifold 545), which is directed at an open doorway 560. In some embodiments, the filter 547 protects the interior components, such as a heat exchanger or coil 567, fans 515, or electronics, from dust and particles.

In some embodiments, the air curtain 505 may be heated. Heated air curtains 505 may have a coil 567 (electric, hot/chilled water, steam, indirect or direct gas, direct expansion, etc.) to heat or cool the jet. Heating may be used to avoid people feeling a cold jet of air when crossing the doorway 560 and also to heat the volume of air coming in at the entrance.

Figure 6:
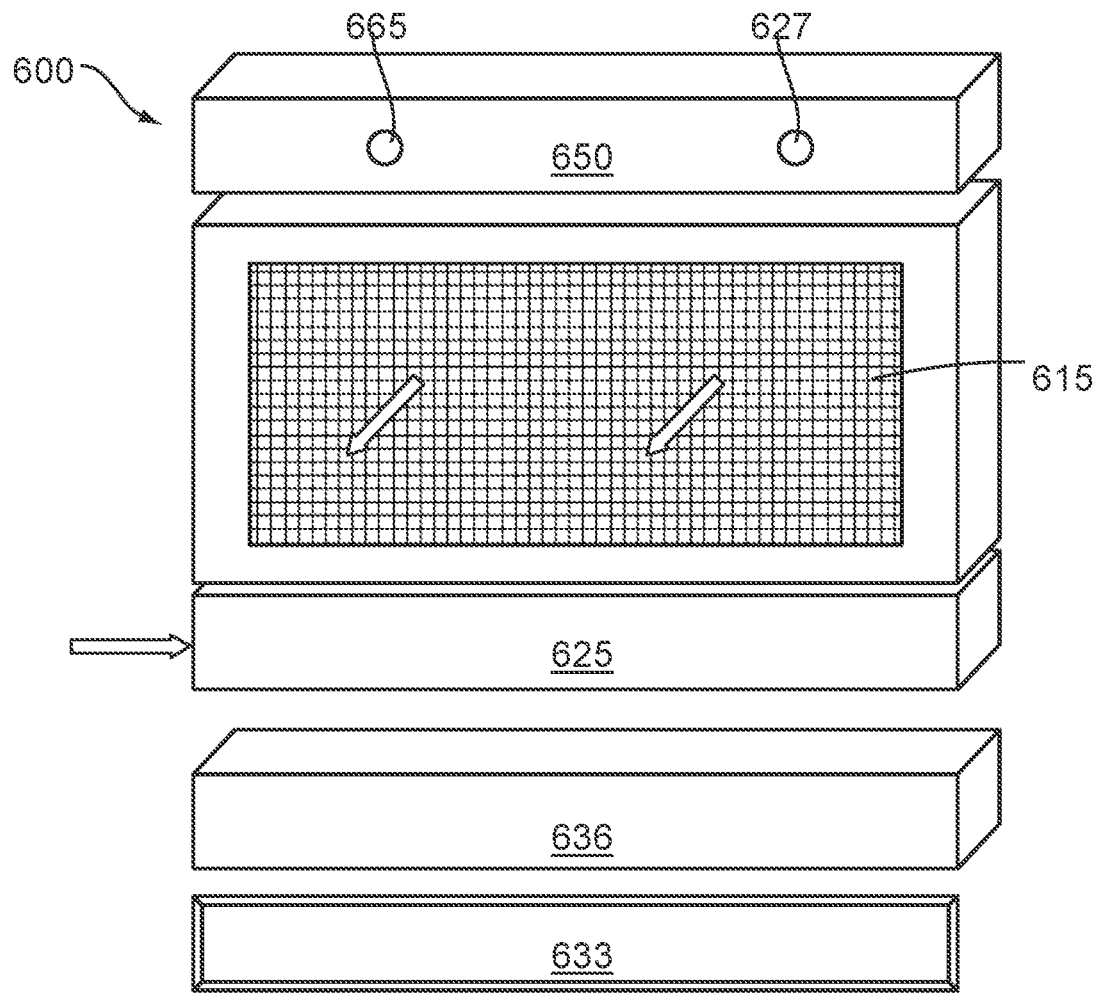
FIG. 6 shows a portable ion generator system in accordance with one embodiment.

FIG. 6 shows a portable ion generator system, herein referred to as an ionizer 600, in accordance with one embodiment. In some embodiments, the ionizer 600 may be an air ionizer designed to decontaminate or disinfect a prescribed area in a prescribed time. For example, in some embodiments, the ionizer may be configured to disinfect an area of 250-500 ft$^2$ in 30-60 minutes.

In some embodiments, the ionizer 600 may be placed in a patient room or screened area after the patient leaves or after a procedure that is likely to generate pathogen-containing aerosols. The ionizer 600 may run for a fixed time duration, after which time the room or area may be safe for the next patient or safe for further cleaning without requiring the use of rated PPE.

In some embodiments, the ionizer 600 may be mounted in the cargo hold of delivery vehicles or a car trunk. In some embodiments, assuming some minimum transit time, the ionizer 600 may provide a measure of protection against transmission via contaminated surfaces on goods or containers. In some embodiments, the ionizer 600 may be temporarily placed or permanently installed in vehicles, such as taxis, police cars, or private vehicles, to provide continuous disinfection of the vehicle cabin.

In some embodiments, the ionizer 600 may perform "hands-off" disinfection of an area, wherein the ionizer 600 completely or nearly eliminates airborne and surface pathogens. This disinfection may be sufficient on its own for some purposes or may be followed up by further, traditional cleaning and disinfection procedures. Treating the area with the ionizer 600 should mitigate the need for cleaning staff to have to don rated PPE in order to safely clean or prepare the room/area.

In some embodiments, the ionizer 600 may have an integrated high-voltage power supply 625 for the ionizer 600. In some embodiments, external power supply 625 may be obtained via at least one of a mains power supply or a rechargeable battery pack 636. In some embodiments, the unit may run off of a USB-C-connected power supply, battery pack, power bank, or an equivalent recognized by a person having ordinary skill in the art.

In some embodiments, the ionizer 600 may further comprise a battery pack 636 or connections for an external battery power source. In some embodiments, battery-powered systems may be operated without connections to mains power. In some embodiments, battery-powered systems may be portable, such that the entire ionizer 600 may be moved and positioned manually. In some embodiments, battery packs 636 may be changed in the field. In some embodiments, the system may be powered by batteries, mains power, or both. In some embodiments, the system may further comprise a mechanism (not shown) whereby an installed battery pack 636 can be charged while the unit is connected to mains power. In one embodiment, the system further comprises at least one indicator 627 to inform the user of the battery charge level and may indicate the approximate number of disinfection cycles remaining for the given battery charge level.

In some embodiments, the ionizer 600 may be coupled to a purpose-built fan unit 615 that is powered from the same power supply 625 as the ionizer 600. In some embodiments, the fan unit 615 may incorporate a rotating base to enhance circulation. In some embodiments, the fan unit 615 and/or rotating base may be integrated with the ionizer 600. Used with the purpose-built fan unit 615, the ionizer 600 may be set on a table or other horizontal surface.

In some embodiments, the ionizer 600 may include a controller and a user interface 650 configured to allow the user to control at least one of power, parameters such as fan speed and ionization, and run time duration. For example, in some embodiments, a user may set the ionizer 600 or fan unit 615 to run for a fixed or customizable time duration.

In some embodiments, the ionizer 600 may comprise a removable metal plate 633 held at an electrical potential opposite from that of the ionizer's output or at ground potential with respect to the ionizer. In some embodiments, the plate 633 may attract and retain pathogen particles in the environment and may be used to assay pathogen presence and/or concentration in an area. In some embodiments, the removable metal plate may be within the ionizer 600 (not shown). In some embodiments, the removable metal plate 633 may be external to the ionizer 600.

Some embodiments may have at least one motion or proximity sensor 665. In some embodiments, when the sensor 665 is activated, the sensor 665 may activate, deactivate, or adjust at least one of the fan speed or the ionizer output based on detected area occupancy or activity levels. In some embodiments, the at least one sensor 665 may be used to extend the battery life of battery-powered portable units. In some embodiments, the at least one sensor 665 may be used to automatically activate disinfection cycles whenever someone enters or leaves a room or area. In some embodiments, the at least one sensor 665 may be used to automatically activate disinfection cycles whenever a door opens or closes. In some embodiments, the sensor 665 may be used to automatically restart the disinfection cycle should someone enter the room (and thus possibly re-contaminate the area). Some embodiments may use at least one sensor 665 to activate the ionizer 600 when an external forced air source is active. For example, a sensor may activate the ionizer 600 when the HVAC's circulation fan is running.

In some embodiments, the portable ionizer 600 may be compatible with a wide range of cleaning and disinfection methods. For example, to disinfect the ionizer 600, a user may wipe-down the ionizer 600 with a disinfectant, use UV irradiation, or clean the ionizer 600 under running water.

Figure 7:
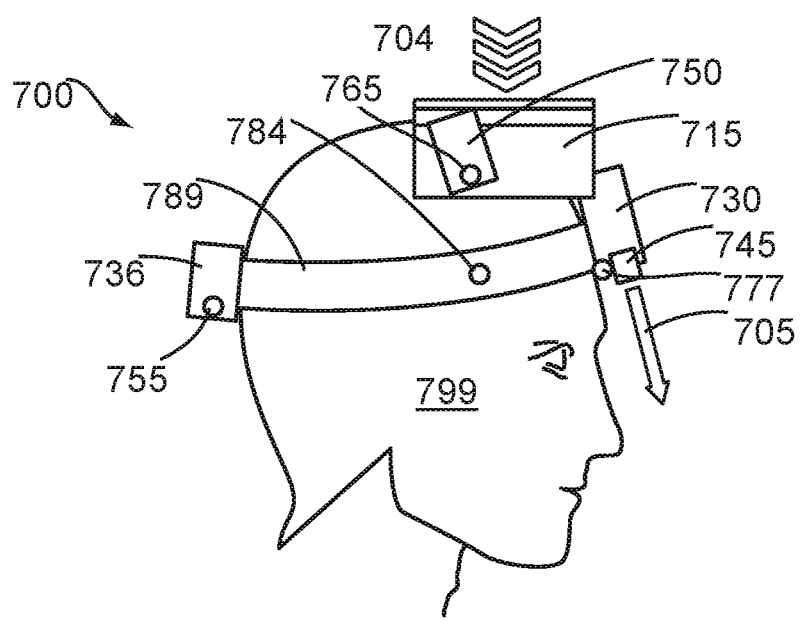
FIG. 7 shows an air ionizer PPA system in accordance with one embodiment.

FIG. 7 shows an air ionizer PPA system 700 in accordance with one embodiment. In some embodiments, the system 700 may include a fan 715, an ionizer 730, a battery pack 736, a laminar output manifold 745, and a control system 750. In some embodiments, the fan 715 is configured to push air 704 through the ionizer 730 and out the laminar output manifold 745 to produce laminar air flow 705. In some embodiments, the fan 715 and the ionizer 730 may be powered by the battery pack 736 and controlled by the control system 750. In some embodiments, the system 700 may be worn on the head 799 or otherwise attached to a user's body or a garment on a user's body. For example, the system 700 may be attached to a headband 789, harness, visor, hat, helmet, or face shield, such that the fan 715 is configured to draw in air 704 in from above the user and direct the ionized output air 705 down and away from the user's face. The action of the fan 715 and the laminar output manifold 745 creates a sheet of ionized air 705 flowing down and away from the user's face.

In some embodiments, the air 705 outputted through the laminar output manifold 745 comprises at least 1 million negative air ions per cubic centimeter of air. In some embodiments, the air 705 outputted through the laminar output manifold 745 comprises at least 10 million negative air ions per cubic centimeter of air. In some embodiments, the air 705 outputted through the laminar output manifold 745 comprises at least 20 million negative air ions per cubic centimeter of air. In some embodiments, the air 705 outputted through the laminar output manifold 745 comprises at least 40 million negative air ions per cubic centimeter of air.

In some embodiments, the PPA system 700 provides protection to both the user and others proximate to the user. In some embodiments, aerosolized pathogen particles may be blown down and away from the user's face and be inactivated by the ionized air 705. In some embodiments, this action provides protection from airborne pathogens to the user and others proximate to the user. In some embodiments, when aerosolized pathogen particles are expelled by the user, such as when breathing, speaking, sneezing, or coughing, the particles will likewise be both inactivated by the ionized air 705 and blown down and away from the user and below the faces of others. In some embodiments, the air 705 passing in front of the user's face has been drawn from above the user's head 799 and is less likely to contain aerosolized pathogen particles than air being drawn at the user's eye level or below.

In some embodiments, the PPA system 700 has no consumables, is essentially infinitely reusable, and provides significant protection to the user, particularly if the user does not have access to a rated respirator. In some embodiments, the PPA system 700 enhances the protection provided by face masks or unrated respirators. In some embodiments, the PPA system 700 may reduce loading of other PPE that the user might be wearing, such as respirators. In some embodiments, the ionized air 705 will act to inactivate virus particles that may collect on such PPE or the user's body, thereby attenuating other transmission vectors.

In some embodiments, the orientation of the laminar output manifold 745 is adjustable. In some embodiments, a user may adjust the angle of the manifold 745 to control the direction of airflow. In some embodiments, a user may adjust the width of the stream of air 705 exiting the manifold 745 to cover a wider or smaller area. In some embodiments, the battery pack 736 may comprise a rechargeable battery and may be interchangeable without removing the PPA system 700 from the head.

In some embodiments, the PPA system 700 may comprise a removable metal plate (not shown) held at an electrical potential opposite from that of the ionizer's output or at ground potential with respect to the ionizer. In some embodiments, this plate may attract and retain pathogen particles that the user encounters and may be used to assay whether the user may have been exposed to the pathogen. In some embodiments, the metal plate may be used to assay to what extent the user may have been exposed to a pathogen. In some embodiments, this is akin to radiation dosimeters worn in radiology labs.

In some embodiments, the PPA system 700 may have a control system 750 comprising switches, buttons, or other mechanisms to allow the user to turn the PPA system 700 on and off, adjust the fan speed, and check the battery charge level. In some embodiments, the control system 750 may further comprise one or more sensors 765 and use sensor data to adjust fan speed, ionizer power, or other parameters based on, for example, relative humidity, wind speed, air temperature, detected contaminant levels, or the user's movement. In some embodiments, the control system 750 is designed to adjust at least one of the fan speed, the ionizer, or the duty cycle such that the expected anion concentration at one or more prescribed locations downstream of the manifold 745 is at or above a prescribed value. Some embodiments may further incorporate one or more light sources 777 such as high-intensity LEDs, such that the PPA system 700 can also serve as a headlamp.

Some embodiments may be designed to be powered from standard military personal power sources in addition to or instead of the battery pack 736 of the PPA system 700.

In some embodiments, the PPA system 700 may be compatible with a wide range of cleaning and disinfection methods. For example, to disinfect the PPA system, a user may wipe-down the ionizer with a disinfectant, use UV irradiation, or clean the ionizer under running water. The PPA system may be used to provide augmented protection for airborne pathogens, dust, smoke, or other airborne matter that is susceptible to ionization.

Portable systems 700 may also be used for infant protection in strollers, infant seats/carriers, baby carriers worn by a parent or caregiver, or in a crib or playpen. Reducing the concentration of active aerosolized pathogens in the area proximate to the infant provides a prophylactic value similar to or better than the protection provided by a typical face mask without disrupting play or creating a choking hazard. Instead of affixing a portable system 700 to a head 799 of a user, some embodiments may affix a portable system to the top, bottom, or side of a baby carriage or playpen, such that a laminar stream of air 705 may exit the manifold 745 to create a partition between the air inside of the carriage and the air outside of the carriage.

In some embodiments, the ionizer 730 in the system 700 is configured to provide a germicidal screen, implemented by flowing ionized air 705, in a compact form-factor that can be readily mounted proximate to a person, including an infant or small child. In some embodiments, the ionizer 730 is configured to output a laminar ionized air curtain configured to create at least a partial barrier between the wearer and external air. In some embodiments, the ionizer 730 may comprise at least one mounting systems, including a headband 789 or strap configured to allow the device to be non-permanently attached to an external mounting point.

In some embodiments, the system 700 may comprise a portable power source, such as a battery pack 736. In some embodiments where a power source is one or more batteries, the system 700 further comprises at least one annunciator 755. In some embodiments, when the battery charge or capacity falls below a prescribed threshold, the annunciator 755 will alert the user with at least one of an audible or visual indicator. In some embodiments, an audible annunciator 755 comprises a buzzer, beeper, or speaker. In some embodiments, a visual annunciator 755 comprises a lamp, light, or a blinking indicator.

In some embodiments, the system 700 may comprise a mounting system such as a spring clip or clamp able to securely attach the device to a mounting point such as a strap, fabric, or panel. In some embodiments, the mounting system may comprise a pin or tack that can be inserted through fabric, webbing, or other materials in like manner to a pin-on nametag or button. In some embodiments, a mounting system comprises the hook or loop side of a hook-and-loop attachment system. In some embodiments, a mounting system comprises at least one of a strap, cord, harness, loop, or lanyard that can be placed or fastened to or around an external mounting point, such as a bar, tube, rail, etc. In some embodiments, a mounting system comprises at least one magnet, with the external mounting point being a ferrous/magnetic material, such as steel or iron.

In some embodiments comprising one or more controls, the device further comprises one or means of temporarily disabling or locking the controls to prevent inadvertent adjustments. In come embodiments, one or more of the controls is designed to be "child-proof", "child-resistant", "child-safe", or equivalent, such that the control is difficult or impossible for a baby or child to actuate. In some embodiments, the device's controls are locked or unlocked by actuating multiple controls simultaneously or by maintaining actuation of one or more controls for a prescribed time duration.

In some embodiments, the system 700 can be configured or operated in a mode wherein the ionizer 730 is energized while the fan 715 is turned off. In this condition, airflow 704 through the device is induced electrostatically by the ionizer 730, providing a continuous, low-velocity flow of ionized air. When air molecules (or other particles) become negatively charged, they are repelled from the one or more anodes in the ionizer 730, which are also at a negative potential. Effectively, air is electrostatically "pumped" through the device.

In some embodiments, the system 700 further comprises one or more communications modules 784 permitting the system 700 to be at least one of wirelessly monitored or controlled from or with an external device. In some embodiments, a communications module communicates with or permits integration with other household wireless products, such as baby monitors, home security systems, and home monitoring systems.

FIG. 8 depicts a bottom view of a germicidal partition system 800 with anodes 830', 830", 830'" (collectively 830) in accordance with one embodiment. In some embodiments, the germicidal partition system 800 comprises a fan 815 configured to direct air over at least one negative ion generator comprising at least one anode 830, at least one high voltage conductor 856, and at least one high voltage source. The negatively ionized air may then travel through the manifold 845 in some embodiments. In some embodiments, the air may travel through the manifold 845 before being directed over at least one anode 830. In some embodiments, the anodes 830 are pointed. In some embodiments, pins are used to direct the air through the manifold 845.

In some embodiments, the airflow, as indicated, is perpendicular to the anodes 830. In some embodiments, the anodes 830 may be parallel to the airflow. The anodes 830 may be located (in the air stream) before the manifold 845, after the manifold 845, inside the manifold 845, or any combination thereof.

In some embodiments, the anodes 830 are connected to a high voltage conductor 856 such that, when connected to a high voltage source (not shown), the air blowing through the manifold 845 comprises at least 1 million negative air ions per cubic centimeter of air.

In some embodiments, the direction of the air is controlled by a laminarizer or other airflow shaping mechanism 866. In some embodiments, a user may be able to adjust at least one of the output of negative air ions, the fan strength, or the direction of the airflow by manually adjusting the system 800 through the control panel 850. In some embodiments, when a sensor receives stimulation, the sensor will adjust at least one of the output of negative air ions, the fan strength, or the direction of the airflow out of the manifold 845.

In some embodiments, the at least one manifold 845 may be removably attached to the system 800, such that the manifold 845 can be removed with the at least one anode 830 from the system 800 and cleaned or exchanged with at least one replacement manifold 845 and at least one replacement anode 830. In some embodiments, the anodes 830 are not integral to the manifold 845 and/or the manifold 845 may not be intended to be replaceable as a unit.

Figure 9:
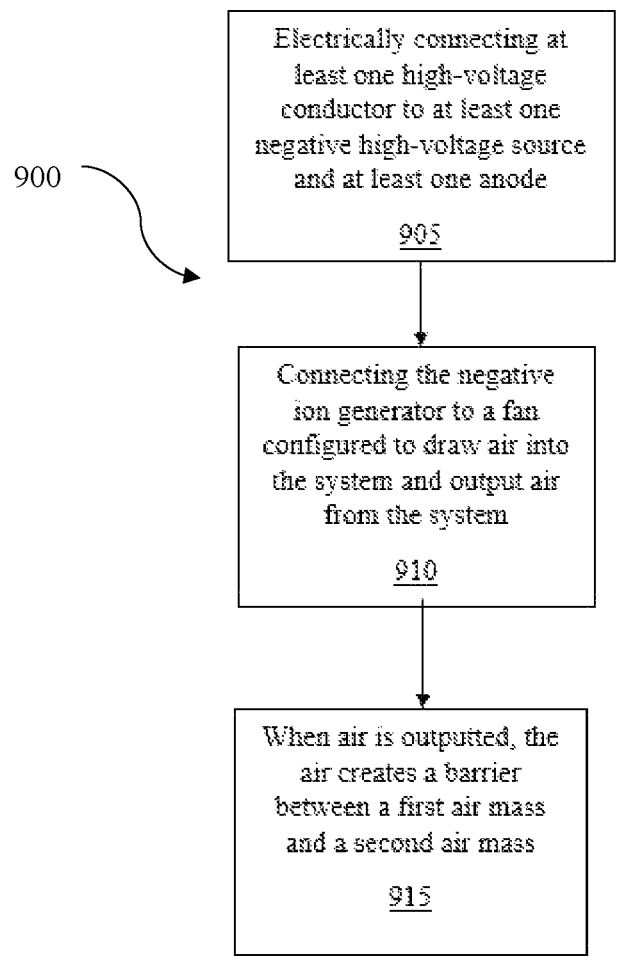
FIG. 9 illustrates a method of building a germicidal partition system in accordance with one embodiment.

FIG. 9 illustrates a method 900 of building a germicidal partition system in accordance with one embodiment. In some embodiments, the method comprises electrically connecting at least one high-voltage conductor to at least one negative high-voltage source and at least one anode 905. In some embodiments, the at least one high-voltage conductor, the at least one negative high-voltage source, and the at least one anode comprise a negative ion generator. The method 900 further comprises connecting the negative ion generator to a fan configured to draw air into the system and output air from the system 910. In some embodiments, the fan is further configured to direct air over at least one anode of the germicidal partition system and output the air through at least one manifold. In some embodiments, the air outputted through the at least one manifold is configured to create a barrier between a first air mass and a second air mass 915, such that the outputted air reduces at least one of the transfer of contaminants or the concentration of viable contagions between the first air mass and the second air mass.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

What is claimed is:

1. A germicidal partition system comprising:
   at least one negative ion generator comprising:
   at least one negative voltage source configured to produce a potential between $-3$ kV and $-10$ kV and sufficient to produce negatively ionized air with a negative air ion concentration of at least 1 million negative air ions per cubic centimeter of air, and configured to produce a net increase in ozone concentration between zero and 0.01 parts per million;
   at least one voltage conductor electrically connected to the at least one negative voltage source;
   at least one output manifold;
   a plurality of anodes distributed along at least a portion of the at least one output manifold and electrically connected to the at least one voltage conductor; and
   at least one fan configured to:
   draw air into the system;
   direct the air into the at least one output manifold and past the plurality of anodes to create the negatively ionized air; and
   output the negatively ionized air through the at least one manifold, wherein the negatively ionized air outputted through the at least one manifold creates a barrier between a first air mass and a second air mass, such that the outputted negatively ionized air reduces at least one of the transfer of contaminants or the concentration of viable contagions between the first air mass and the second air mass; and
   wherein the output manifold can be rotated about an axis approximately perpendicular to the direction of airflow, or such that the manifold can be rotated about an axis approximately parallel to the direction of airflow wherein the first air mass comprises air inside a transportation device and the second air mass comprises air outside of the transportation device at, and the germicidal partition system further includes at least a first door position sensor in communication with a control system to monitor a position of a door of a transportation device and configured to, upon detecting that the door has been closed for a specified duration of time, alter a state of at least one manifold, a vane or diverter, or a diffuser, such that at least some of the negatively ionized air output is directed away from the door.

2. The system of claim 1 further comprising:

at least one sensor, and at least one annunciator, wherein:

the at least one sensor is in operable communication with the control system, the control system is in operable communication with the at least one annunciator, and the control system is configured to:

configure the annunciator into a first state upon receiving a stimulus, and configure the annunciator into a second state upon expiration of a specified time duration.

3. The system of claim 2 wherein the at least one sensor is configured to be stimulated by at least one of motion, proximity, sound, contact, a switch, a digital signal, an analog signal, a radio or radio frequency signal, light, imagery, or processed imagery.

4. The system of claim 1 wherein the system is configured to mechanically or electrically connect with or to communicate with a second system.

5. The system of claim 1 wherein the transportation device is an elevator.

6. The system of claim 1 wherein the system is configured to create a barrier between a first designated sitting or standing area and a second designated sitting or standing area.

7. The system of claim 1 wherein at least one output manifold is configured to direct at least some negatively ionized air at one or more angles divergent from the barrier.

8. The system of claim 1 further comprising at least one light source configured to illuminate at least part of an area subtended by the barrier when the system is activated or when the system is active and the illuminated subtended area is readily-discernable by a viewer.

9. The system of claim 1 wherein the system is configured with a mounting system including at least a first attachment point to enable the system to be integrated with, or installed in, on, the transportation device.

10. The system of claim 9 wherein the first attachment point is configured to be removably attached to and mechanically supported by a first adapter.

11. The system of 10 wherein at least one of removing the system from or mounting the system to the first adapter does not require tools or does not require modifications to the first attachment point of the system.

12. The system of claim 10 wherein the first adapter is attached to a first object, at least a second adapter is attached to a second object, and the system is configured to be removed from the first adapter and mounted on the second adapter.

13. The system of claim 9 further comprising at least one fan, wherein the control system is programmed to alter the state of the speed of the at least one fan to prescribed speeds according to the detection of movement proximate to the system, movement of the system, of the presence or non-presence of a person or an object at least one prescribed location, of prescribed sounds or sound pressure levels originating from at least one prescribed location or direction relative to the system, ambient light levels, or the dimensions or geometry of the area downstream of the at least one manifold.

14. The system of claim 9 wherein the system is configured such that the output manifold can be adjusted or reconfigured to direct at least some negatively ionized air towards an occupant of the transportation device.

15. The system of claim 1 further comprising least one grounding conductor, wherein the at least one grounding conductor is electrically connected to a negative input voltage reference, a negative battery terminal, or the ground reference of the negative voltage source.

16. The system of claim 1 wherein the output manifold can be rotated about an axis approximately perpendicular to the direction of airflow and relative to at least one other component of the germicidal partition system such that the at least one other component of the germicidal partition system remains stationary, or rotated about an axis approximately parallel to the direction of airflow and relative to at least one other component of the germicidal partition system such that the at least one other component of the germicidal partition system remains stationary.

* * * * *